United States Patent [19]
Cavell et al.

[11] Patent Number: 5,334,791
[45] Date of Patent: Aug. 2, 1994

[54] HYDROGENATION PROCESS WITH TRANSITION METAL CATALYSTS DERIVED FROM BIFUNCTIONAL PHOSPHORUS-NITROGEN LIGANDS

[75] Inventors: Ronald G. Cavell; David J. Law, both of Edmonton; Robert W. Reed, Guelph, all of Canada

[73] Assignee: Ligands Inc., Calgary, Canada

[21] Appl. No.: 887,014

[22] Filed: May 22, 1992

[51] Int. Cl.$^5$ ............................................. C07C 5/03
[52] U.S. Cl. ............................ 585/277; 585/275; 585/276; 502/166; 502/167
[58] Field of Search .................... 585/275, 276, 277; 502/166, 167

[56] References Cited

U.S. PATENT DOCUMENTS

| | | |
|---|---|---|
| 3,454,644 | 7/1969 | Dewhirst . |
| 3,849,490 | 11/1974 | Vogt et al. . |
| 3,978,101 | 8/1976 | Aviron-Violet . |
| 4,119,652 | 10/1978 | Knowles et al. . |
| 4,166,824 | 9/1979 | Henderson et al. . |
| 4,397,787 | 8/1983 | Riley . |
| 4,440,936 | 4/1984 | Riley . |
| 4,668,651 | 5/1987 | Billig et al. ........................ 502/158 |
| 4,743,699 | 5/1988 | Page et al. . |
| 4,769,498 | 9/1988 | Billig et al. ........................ 568/454 |
| 4,857,235 | 8/1989 | Heggie et al. . |
| 4,863,639 | 9/1989 | Heggie et al. . |
| 4,911,865 | 3/1990 | Heggie et al. . |
| 4,999,443 | 3/1991 | Bertlett et al. . |

FOREIGN PATENT DOCUMENTS

| | | | |
|---|---|---|---|
| 0283616 | 9/1988 | European Pat. Off. ........... | 502/166 |
| 0061937 | 5/1980 | Japan ................................ | 502/166 |
| 0253996 | 2/1988 | Japan ................................ | 502/166 |

OTHER PUBLICATIONS

J. Chatt et al., "Olefin Co-ordination Compounds. Part VI. Diene Complexes of Rhodium," *J. Chem. Soc.* (1957) 4735–41.

Lee et al., "Synthesis and Characterization of Dinuclear Palladium (I) and Mononuclear Paladium (II) Complexes Containing 1,1-Bis(diphenylphos-phino)ethane (dpmMe) and Related Mixed-Ligand Complexes Containing dpmMe with Either (Bis(diphenylphos-phino)methane (dpm) or 2-(Diphenylphos-phino)pyridine (Ph$_2$Ppy). X-ray Crystal Structures of PdCl$_2$(dpmMe) and Pd$_2$Cl$_2$($\mu$-dpmMe)$_2$," *Organometallics* 5 (1986) 2220–28.

Tunney et al., "Palladium-Catalyzed Coupling of Aryl Halides with Tri–" *J. Org. Chem.*, vol. 52, No. 5 (1987), pp. 748–753.

Hassner et al., "Synthesis of Alkyl Azides with a Polymeric Reagent," *Angew. Chem. Int. Ed. Engl.* 25 (1986), No. 5, 478–79.

Keana et al., "Functionalized Perfluorophenyl Azides: New Reagents for Photoaffinity Labeling," *Journal of Fluorine Chemistry* 43 (1989) 151–54.

Katti et al., "Two Novel Rhodium(I) Metallacycles from the New Heterodifunctional Ligand Me$_3$SiN=PPh$_2$CH$_2$PPh$_3$. An Example of the Formation of a Unique Iminato Nitrogen-Rhodium $\sigma$ Bond," Organometallics, vol. 7, No. 10 (1988), 2236–38.

Katti et al., "First Examples of an Ismeric Methylene--Bridged Free Phosphano Phosphoranimine and a Metalated Phosphano Phosphoranimine. Synthesis, Characterization, and Isomerization of the Heterodifunctional (List continued on next page.)

Primary Examiner—Asok Pal
Attorney, Agent, or Firm—Millen, White, Zelano, & Branigan

[57] ABSTRACT

A process is provided for hydrogenating a non-aromatic unsaturated hydrocarbon, comprising reacting the hydrocarbon with a catalyst precursor which includes a source of a group VIIIB transition metal from the second or third rows of the periodic table and a heterobifunctional ligand constructed with a phosphine center and an imine nitrogen center, in the presence of hydrogen and a promoter selected from secondary or tertiary acyclic alkyl amines in a suitable solvent which solubilizes the hydrocarbon, the catalyst precursor, the hydrogen, and the promoter.

18 Claims, 2 Drawing Sheets

OTHER PUBLICATIONS

Ligand ($\eta^3$-C$_5$H$_5$TlCl$_2$NPPh$_2$CH$_2$PPh$_2$)," *Inorganic Chemistry*, vol. 28, No. 3 (1989) pp. 413–416.

Katti et al., "New Approaches to Heteroatomic Chelation of Early and Late Transition Metals. Synthesis and Characterization of Cyclometalla-phosphoranimine- and Cyclometallaphosphoraniminatophosphanes (and rsanes) of Mo(O), W(O), Rh(I), and Ir(I) Derived from Novel Heterodi-functional Phosphorus and Arsenic Ligands," *Organometallics*, vol. 8, No. 9 (1989), 2147–53.

Moloy et al., "Rhodium–Catalyzed Reductive Carbonylation of Methanol," *Organometallics*, vol. 8, No. 12 (1989), 2883–92.

"Carbonylation of Methanol at Unusually Low Temperature and Pressure with cis-PhCl(CO)$_2$Ph$_2$P(CH$_2$)$_2$," *J. Chem. Soc. Commun.*, 1987, 1891–92.

Cavell et al., "Potential Catalytic Systems Derived from Metal Complexes of a New Heterobifunctional Ligand," *Programme and Information,* Sixth International Symposium on Homogenous Catalysis, Aug. 21–26, 1988, Vancouver, British Columbia, Canada.

J. A. Osborn, F. H. Jardine, J. F. Young, G. Wilkinson: J. Chem. Soc. (A) (1966) 1711.

R. R. Schrock and J. A. Osborn, J. Am. Chem. Soc., 98 (1976) 2143.

R. H. Crabtree, A. Gautier, G. Biordano and T. Kan: J. Organomet. Chem. 141 (1977) 113.

J. Halpern and C. R. Landis: Organomet. Chem., 250 (1983) 485.

J. Halpern: Phosphorous and Sulfur, 18 (1983) 307.

G. Wilkinson, P. S. Hallman and B. R. McGarvey: J. Chem. Soc. (A) (1968) 3143.

R. H. Crabtree, H. Felkin and G. E. Morris: J. Organomet. Chem., 141 (1977) 205.

R. H. Crabtree, Acc. Chem. Res. 12 (1979) 331.

J. M. Brown, Angew. Chem. Int. Ed. Engl. 26 (1987) 190.

W. S. Knowles, Acc. Chem. Res. 16 (1973) 106.

COMPOUND TYPE C

COMPLEX TYPE B

COMPLEX TYPE A $Q = CH_2, \ C(H)CH_3, \ CH_2CH_2,$ $R = SiMe_3,$

HYDROGENATION PROCESS WITH TRANSITION METAL CATALYSTS DERIVED FROM BIFUNCTIONAL PHOSPHORUS-NITROGEN LIGANDS

FIELD OF THE INVENTION

This invention relates to a hydrogenation process for non-aromatic unsaturated hydrocarbons using catalyst precursors based on a group VIIIB transition metal and a phosphine ligand.

BACKGROUND OF THE INVENTION

Homogeneous hydrogenation catalysts for the production of hydrogenation reactants are well known in the art, with many systems being based on rhodium metal combined with phosphine ligands. Examples of such catalysts were first described in J. A. Osborn, F. H. Jardine, J. F. Young and G. Wilkinson, *J. Chem. Soc.* (A) (1966) 1711.

The Osborn et al. paper describes tile hydrogenation of hydrogenatable products using a catalyst precursor of the formula [RhCl(PPh$_3$)$_3$] and a pressure of hydrogen gas of one atmosphere, this system presently remains the catalyst of choice for many homogeneous hydrogenation applications even though it has not ken optimized or improved despite considerable efforts to do so. One disadvantage of this system is that it has low selectivity in the hydrogenation of different hydrogenatable sites within the same reactant.

In an effort to improve on this system work described in R. R. Schrock and J. A. Osborn, *J. Am. Chem. Soc.*, 98 (1976) 2143 employed catalyst precursors of the general formula [Rh(diene)L$_n$]+X− (where "client" is a hydrocarbon diene such as cyclooctadiene or norbornadiene, L=tertiary phosphine, n=2, X−=ClO$_4$−, BF$_4$−, PF$_6$−. Only a moderate improvement in reactivity ascribed to the use of coordinating solvents was demonstrated in this work. Also of note was that the more basic tertiary phosphine ligands, e.g., PPhMe$_2$ promoted the hydrogenation rates but also promoted the isomerization of the reactants. For example, 1-hexene is readily isomerized to cis- and trans-2-hexene under the, conditions employed.

The use of this catalytic system utilizing non-coordinating solvents is described in R. H. Crabtree, A. Gautier, G. Biordano and T. Khan *J. Organomet. Chem.* 141 (1977) 113 where catalyst precursors of the general formula [Rh(cod)L$_2$]+PF$_6$−(cod=Cyclooctadiene, L=tertiary phosphine or amine) in dichloromethane solvent gave significant improvement in catalytic activity over the results reported by Schrock and Osborn op. cit. In the work of Crabtree et al. the highest reactivity was obtained using the complex [Rh(cod)(PPh$_3$)$_2$]+PF$_6$− in dichloromethane solvent, particularly for the hydrogenation of 1-hexene to hexane.

Following this work further reactivity improvements were reported in J. Halpern and C. R. Landis, *J. Organomet. Chem.*, 250 (1983) 485 and J. Halpern, *Phosphorus and Sulphur*, 18 (1983) 307 wherein complexes of the general formula [Rh(diolefin)P$_2$]+X− were employed as catalyst precursors (P$_2$=a chelating bis-tertiary phosphine ligand, X−=a non-coordinating anion, typically BF$_4$−). It was found that the use of chelating bis-phosphine ligands of the type Ph$_2$P(CH$_2$)$_n$PPh$_2$ (where n=2, 3, 4, 5) gave significant enhancement of catalytic activity particularly when n=3 or 4.

Therefore it is noted that the reactivity of rhodium-phosphine catalysts in homogeneous hydrogenation can depend strongly on the solvent choice and on the nature of the phosphine ligand.

Metals other than rhodium have been employed in catalytic homogeneous hydrogenation utilizing phosphine complexes of those metals.

An example of such a catalyst is given in G. Wilkinson, P. S. Hallman and B. R. McGarvey *J. Chem. Soc.* (A) (1968) 3143 where a compound of the formula [RuHCl(PPh$_3$)$_3$] was shown to be an active catalyst for the hydrogenation of terminal alkenes such as 1-hexene but was a poor catalyst for hydrogenation of internal or cyclic alkenes such as cyclohexene. Similar such compounds containing ruthenium or osmium have been reported in U.S. Pat. No. 3,454,644.

Another example of such catalysts is the use of iridium in R. H. Crabtree, H. Felkin and G. E. Morris *J. Organomet. Chem.*, 141 (1977) 205 and R. H. Crabtree, *Acc. Chem. Res.* 12 (1979) 331 where compounds of the general formula [Ir(cod)L$_2$]+PF$_6$− (L=tertiary phosphine or amine) in dichloromethane solvent where found to be highly active hydrogenation catalyst for all types of alkene reactants.

A review covering applications of some of the previously mentioned catalyst precursors deemed to be the state of the art can be found in J. M. Brown, *Angew. Chem. Int. Ed. Engl.* 26 (1987) 190 which include particularly the catalyst precursors having the formulae [RhCl(PPh$_3$)$_3$], [Rh(nbd)dppb]+BF$_4$− and [Ir(cod)PCy$_3$(Py)]+PF$_6$−(nbd=2,5 norbornadiene, dppb=1,4 bisdiphenylphospinobutane, cod=1,5 cyclooctadiene Cy=cyclohexyl and Py=pyridine).

Also of note is the use of chiral bis tertiary diphosphines in asymmetric hydrogenation with rhodium(I) catalyst precursors. Coverage of this application in both industrial and laboratory processes is given along with many related references in W. S. Knowles, *Acc. Chem. Res.* 16 (1983) 106 and H. B. Kagan, *Bull. Soc. Chim.*, 5 (1988) 846. Interest in this area of hydrogenation has been intense and there are a number of patents related to synthesis and application of several rhodium-chiral diphosphine catalyst precursors: U.S. Pat Nos. 3,419,907; 3,849,490; 3,878,101; 4,166,824; 4,119,652; 4,397,787 and U.S. Pat. No. 4,440,936.

A number of rhodium-phosphine and rhodium-phosphite catalyst precursors have appeared in patent literature many of which are designed only to carry out specific hydrogenations of a specific reactant: U.S. Pat. Nos. 4,999,43, 4,911,865, 4,857,235, 4,863,639 and U.S. Pat. No. 4,743,699.

SUMMARY OF THE INVENTION

This invention provides a process for hydrogenating a non-aromatic unsaturated hydrocarbon, comprising reacting the hydrocarbon with a catalyst precursor which includes a source of a group VIIIB transition metal from the second or third rows of the periodic table and a heterobifunctional ligand constructed with a phosphine center and an imine nitrogen center, in the presence of hydrogen and a promoter selected from secondary or tertiary acyclic alkyl amines, in a suitable solvent which solubilizes the hydrocarbon, the catalyst precursor, the hydrogen, and the promoter. Rh(I) is the preferred transition metal. Preferred catalyst precursors are selected from the general formulae I, II, or III

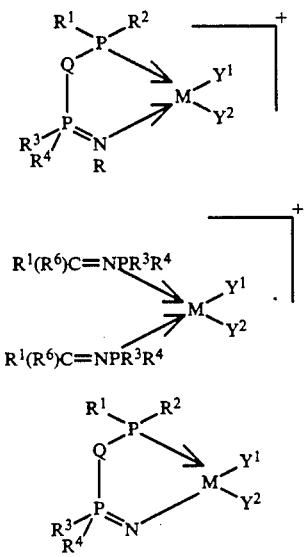

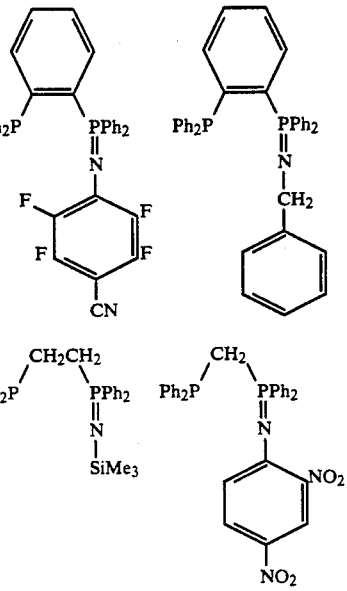

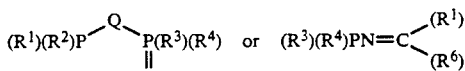

and preferred ligands are of general formulae I' and II'

$$(R^1)(R^2)P\overset{Q}{\underset{\underset{NR}{\parallel}}{-}}P(R^3)(R^4) \quad \text{or} \quad (R^3)(R^4)PN=C\overset{(R^1)}{\underset{(R^6)}{\diagdown}}$$

I'  II' where in the above formulae;

R$^1$–R$^4$ = same or different, substituted or unsubstituted, alkyl, aryl, alkoxide, aryloxide, amino, or thiol groups Y$^1$, Y$^2$ = same or different, olefinic hydrocarbons Q = (CH$_2$)$_n$, n = 1–5, benzene ring connected to the P atoms in the ortho positions, an olefin connected to the P atoms in the cis position, C(H)CH$_3$ and a substituted amine N(R$^7$)

R$^6$ = hydrogen or the substituents as defined for R$^1$–R$^4$ above

R$^7$ = substituted or unsubstituted, aryl or alkyl

M = Group VIIIB transition metal from the second or third row of the periodic table R = Si(CH$_3$)$_3$ , substituted or unsubstituted benzyl, and

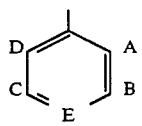

where A,B,C,D are the same or different and selected from F, H, NO$_2$ and alkyl, E is endocyclic nitrogen, C-CN or isomers thereof.

Preferably the catalyst precursor is formed in situ from a mixture of a Rh(I) compound and the ligand. In this case preferred ligands include formulae I' and II' set out herein above. More preferably the ligands include I' and II' where R$^1$ = R$^2$ = R$^3$ = R$^4$ = Ph, R$^6$ = H, Q = CH$_2$, C$_2$H$_4$, C(H)CH$_3$, o-C$_6$H$_4$, and R = Si(CH$_3$)$_3$, C$_6$F$_4$CN, benzyl and 2,4-C$_6$H$_4$(NO$_2$)$_2$. Preferred Rh(I) source compounds are Rh(I) halogen diolefin complexes such as [RhCl(cod)]$_2$, [RhCl(nbd)]$_2$ or [RhCl(C$_2$H$_4$)$_2$]$_2$, where cod = 1,5 cyclooctadiene and nbd = norbornadiene, being non-limiting examples.

The most preferred solvent includes ethanol.

The preferred promoter is triethylamine, diethylamine or mixtures thereof.

The invention also broadly extends to the novel heterobifunctional ligands:

Figure 1A:
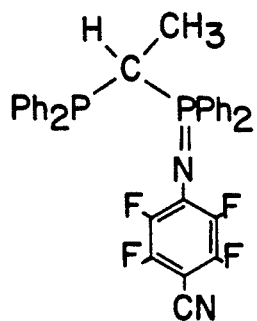
FIG. 1 is a formula sheet for the exemplary catalyst precursor ligands of the present invention.
Figure 1B:
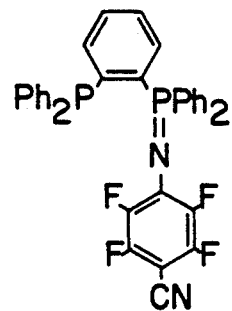
Figure 1C:
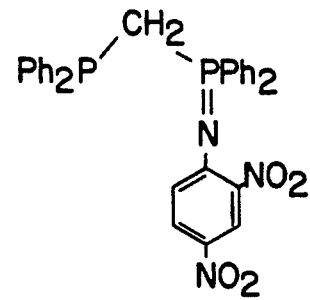
Figure 1D:
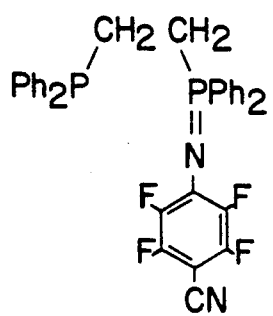
Figure 1E:
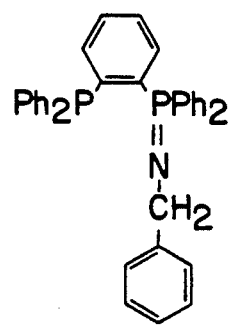
Figure 1F:
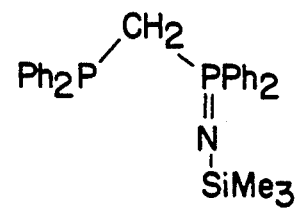
Figure 1G:
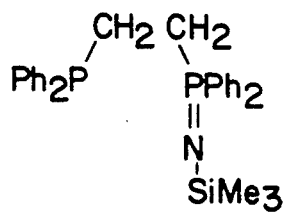
Figure 1H:
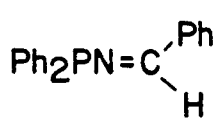

The following are the chemical nomenclature of the compounds with the structural formulas represented by FIGS. 1a to 1h:

1a  1-(N-4-cyanotetrafluorophenyl-diphenylphosphinimine-1-diphenylphosphino)ethane 1b  1-(N-4-cyanotetrafluorophenyldiphenylphosphanimine-2-diphenylphosphino)benzene 1c  N-2, 4-di(nitro)phenyl(diphenylphosphoranimine)-methylene diphenylphosphine 1d  1-(N-4-cyanotetrafluorophenyl-diphenylphosphinimine-2-diphenylphosphino)ethane 1e  1-(1,2-phenylene(diphenylphosphoranimine)-2-diphenylphosphino)benzene 1f  1,diphenylphosphino-1, (N-trimethylsilyldiphenylphospinimine)methane 1g  1,diphenylphosphino-2, (N-trimethylsilyl)diphenylphosphinimine)ethane 1h  N-diphenylphosphinobenzalmine.

Figure 2:
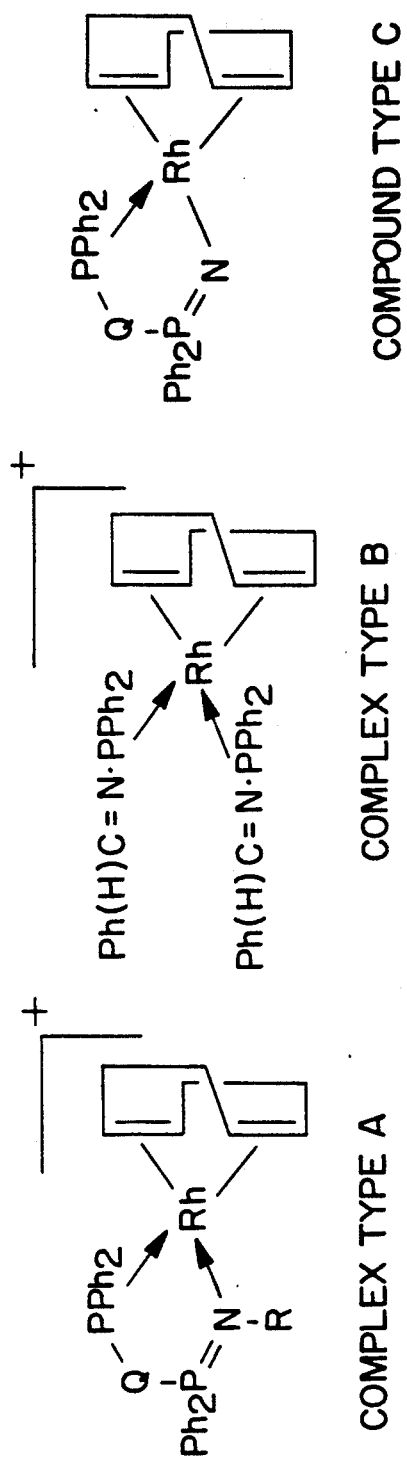
Figure 2:
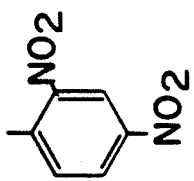
Figure 2:
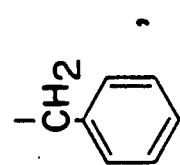
Figure 2:
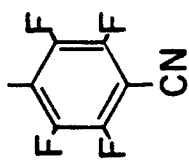

FIG. 2 is a formula sheet for the exemplary catalyst precursor complexes and compounds of the present invention.

DESCRIPTION OF THE PREFERRED EMBODIMENTS

Hydrogenation Catalyst System and Its Preparation.

In accordance with the preferred process of the present invention, hydrogenated products are produced by reaction of a hydrogenatable reactant, generally a non-aromatic unsaturated hydrocarbon such as olefins, and hydrogen with a rhodium component Rh(l), and a heterobifunctional phosphorus/nitrogen containing ligand component (PN). When combined with the rhodium component (Rh), the ligand forms a compound or complex of rhodium with the phosphorus-nitrogen substituent and thus forms the metal based portion of the catalytically active system. A nitrogen containing promoter component, which is selected from a tertiary or secondary acyclic alkyl amine is also essential to the operation of the system. The hydrogenation process is conducted in a suitable solvent which solubilizes the reactants, catalyst precursors and promoter but which does not interfere significantly with the hydrogenation process. Ethanol alone or mixed with other suitable solvents is preferred.

The rhodium source (Rh) for the assembly of the catalytically active component of the catalyst system can be provided by any material which will produce a coordinatively unsaturated rhodium complex under the catalyst conditions. Preferred materials to produce the rhodium containing component of the catalyst system in the present invention are typically rhodium halogen diolefin complexes such as $[RhCl(cod)]_2$, $[RhCl(nbd)]_2$ or $[RhCl(C_2H_4)_2]_2$, where cod=1,5 cyclooctadiene and nbd=norbornadiene, being non-limiting examples.

The rhodium-containing catalytically active component of the present invention may be supplied from a pre-preparation in which components of (Rh) and the (PN) ligand are united by means of a direct reaction of the appropriate constituents or by the separate supply of the components (Rh) and (PN) upon assembly of the reaction system (i.e. by in situ formation of the catalyst precursor).

The ligands which are effective have a structure which provides two reactive sites of different chemical character (such as, but not exclusively, "hard" and "soft" reactivities) such as are provided by a phosphine phosphorus and a nitrogen base (such as an imine functionality of a phosphine imine). Examples are illustrated in the attached FIG. 1. The ligands may act to form complexes by the coordination of both phosphorus and nitrogen to form a chelate such as is illustrated as Complex types A and B in the attached FIG. 2 or the ligand may eliminate a reactive substituent such as $Me_3Si$ in the form of $Me_3SiCl$ by means of action with at metal halide so as to form a metal-nitrogen o- bond binding the bifunctional ligand to the metal such as is illustrated by compound type C in the attached FIG. 2.

The preferred reaction conditions for the present invention are typically ambient temperatures and pressures of hydrogen, typically 20°-25° C. and 1.0 to 1.1 atmospheres pressure.

For opimum activity of the catalytic system of the present invention a rhodium to ligand ratio of 1 to 1 is preferred. Ratios of ligand to rhodium that are either lower or that exceed this optimum ratio tend to impede catalytic activity as demonstrated in the examples. However the exact ratio of metal to ligand that totally impedes catalysis from taking place is likely to be ligand dependant and is not predictable for all the ligands of the present invention.

It will be noted, that catalysis is an inexact science, an empirical art, unenlightened by rules decreeing certainty and predictability. Therefore it follows that the actual catalyst formed under hydrogenation conditions utilizing stated components may be different from the initially formed coordination compound of rhodium or rhodium catalyst precursor. In fact it is possible that several such catalytic species may be present and may in fact be, in whole or in part, the actual active catalyst component or components.

The preferred pre-preparation of the rhodium containing catalytically active component involves the reaction of a rhodium chloride diolefin compound (Rh) with a phosphoraniminatophosphine ligand (PN) and a counter ion source such as $KPF_6$ which will yield a rhodium compound of the type [Rh(diolefin)-(ligand)]$^+PF_6^-$ through the elimination of potassium chloride. Other counter ion sources such as $KClO_4$ and $KBF_4$ are equally useful for this preparation.

The hydrogenatable reactants suitable for use in the present invention are those compounds capable of undergoing hydrogenation under hydrogenation conditions to yield hydrogenation products. Particularly preferred materials include those selected from the group of compounds having the formula (a) $R^1$—CH=$CH_2$ ($R^1$=alkyl, aryl)
(b) $R^2$—CH=CH—$R^3$ ($R^2$=alkyl, aryl, $R^3$=alkyl, aryl) ($R^2$ and $R^3$, together with CH=CH, form a non-aromatic unsaturated hydrocarbon ring having 6 carbon atoms or more.)
(c) $R^2$—CH=$CR^1$ $R^2$ (Where $R^2$, $R^2$ and $R^2$ are as above.)

Non-limiting examples of hydrogenatable reactants defined under (a), (b) and (c) include hex-1-ene, cyclohexene, styrene and 1-methyl cyclohexene.

EXPERIMENTAL

General considerations for preparation of complexes and ligands

All experimental manipulations were performed under an atmosphere of dry argon. Solvents were dried and distilled prior to use. [Rh(cod)Cl]$_2$ was prepared by standard procedures.[J. Chart and L. M. Venanzi, *J. Chem. Soc* (1957) 4735]. Unless otherwise specified ligands were prepared as described in co-pending U.S. patent application 07/752,348 filed (Sep. 3, 1991) and in published PCT patent application PCT/CA/91/00309 filed Aug. 30, 1991 (publication number WO 92/04118) by Cavell et al., which applications are hereby incorporated by reference.

$^1$H and $^{31}$p NMR spectra were obtained on a Bruker WH400 instrument (operating at 400.13 and 161.97 MHz, respectively) using $SiMe_4$ and 85% $H_3PO_4$ as external standards. In all spectroscopic studies $CD_2Cl_2$ was used as both solvent and internal lock. Positive shifts lie downfield of the standard in all cases.

Preparation of ligand 1a: [1-(N-4-cyanotetrafluorophenyl-diphenyphosphinimine-1-diphenylphosphino)ethane], Into a 250 mL side-arm round bottom flask was placed 3.28 g(8.24 mmol) of 1,1-bis(diphenylphosphino)ethane [C. L. Lee, Y. P. Yang, S. J. Rettig, B. R. James, D. A. Nelson, M. A. Lilga. *Organometallics* 5 (1986) 2220] and 50 cm$^3$ of dry $CH_2Cl_2$ The solution was cooled to −78° C. and 1.77 g (8.19 mmol) of 4-cyclotetrafluorophenyl azide [J. F. W. Keana and S. X. Cal. *J. Fluorine Chemistry* 43 (1962)151 ] in 30 cm$^3$ of $CH_2Cl_2$ was added dropwise. The reaction solution immediately developed a yellow colour. The solution was allowed to stir and warm slowly to room temperature overnight. Removal of the solvent in vacuo followed by recrystallization from acetonitrile produced 3.55 g (6.05 mmol) of large white blocks of Ligand 1.

M.P.=178°-180° C.

Analysis: $C_{33}H_{24}F_4N_2P_2$; Calculated: C=67.58, H=4.12, N=4.78%; Found: C=67.24, H=4.27, N=4.78%. I. R. ($CH_2Cl_2$ cast, cm$^{-1}$) 3080w, 2230s, 1645s, 1510vs br, 1435s, 1325w, 1310w, 1300w, 1290w, 1265w, 1220s, 1185w, 1160w, 1110s, 1010m, 980s, 865m, 740s, 695s, 575m, 525s, 505m. M. S. M+ = 586 (3%). $^1$H NMR ($\delta$, CDCl$_3$, TMS) 7.50 ppm, m, 20H; 3.75 ppm, doublet of sextets, 1H; 1.20 ppm, m, 3H. $^{31}$NMR ($\delta$, CDCl$_3$, H$_3$PO$_4$) 21.9 ppm. dt, $^2J_{pp}$=67.8 Hz, $^4J_{PF}$=4.2 Hz.; −14.8 ppm, d, $^2J_{pp}$=68.0 ppm. $^{19}$F NMR ($\delta$, CDCl$_3$, C$_6$F$_6$) −139.3 ppm, m; −152.0 ppm, m.

Preparation of Ligand 1b:[1-(N-4-cyanotetrafluorophenyldiphenylphosphanimine-2-diphenylphosphino)-benzene]

To a chloroform solution (30 cm$^3$) of ortho-bis(diphenylphosphino)benzene [S. E. Tunney and J. K. Stille, *J. Org. Chem.*,52,(1987) 748] (1.81 g, 4.05 mmol) at 0° C. was added dropwi 0.95 g (4.40 mmol) of 4-CN-C$_6$F$_4$-N$_3$ in 20 cm$^3$ of chloroform. The reaction was complete in one hour as determined by $^{31}$p NMR spectroscopy. The reaction mixture was stirred overnight and then the solvent was removed in vacuo. Recrystallization from acetonitrile produced 2.20 g (3.47 mmol, 86%) of fine, off-white crystals of Ligand 2.

M.P.=211°-213° C.

Analysis: C$_{37}$H$_{24}$F$_4$P$_2$N$_2$. Calculated: C=70.04, H=3.81, N=4.41%. Found: C=69.84, H=4.02, N=4.26%. I.R. (CH$_2$Cl$_2$ cast): 3055w, 2225w, 1647m, 1502s, 1433m, 1230m, 1103w, 1050s br, 980s, 7.39w, 734m, 715m, 690s, 528vs, 511w, 505w, 492m. M.S.: M+=634 (23%), 557 (100%). $^1$H NMR ($\delta$, CDCl$_3$, TMS) phenyl groups 8.0-7.0 ppm, $^{31}$P NMR ($\delta$, CDCl$_3$, H$_3$PO$_4$) 11.88 ppm, dt, $^3J_{pp}$=21.0 Hz, $^4J_{PF}$=4.54 Hz; −14.84 ppm, d, $^3J_{pp}$=20.8 Hz. $^{19}$F NMR ($\delta$, CDCl$_3$, C$_6$F$_6$) −139.4 ppm, m; −151.7 ppm, m.

Preparation of Ligand 1c [N-2,4-di(nitro)phenyl(diphenylphosphoranimine)methylene diphenylphosphine]

To a solution of (CH$_3$)$_3$SiN=PPh$_2$CH$_2$PPh$_2$(3.72g; 7.90 mmol) in dry toluene (100 cm$^3$) was added dropwise a solution of C$_6$H$_3$(NO$_2$)$_2$F (1.47 g; 7.93 mmol) also in toluene (50 cm$^3$). The reaction mixture was refluxed for 12 hour before the solvent was removed in vacuo to leave a yellow crystalline solid. This crude product was crystallized from acetonitrile to obtain the pure ligand 3 (yield 4.0 g, 90%; yellow crystals; m.p. 198° C.)

Anal. calcd for C$_{31}$H$_{25}$N$_3$O$_4$P$_2$: C,65.95;H,4.43;N,7.44 Found: C,66.00; H,4.40; N,7.46%, MS(EI,m/z): 564(M+, 100%). $^1$H NMR (CDCl$_3$) phenyl rings $\delta$7.20, 7.56, 7.80 (m,20H); PCH$_2$P methylene $\delta$3.35(d,2H,$^2J_{HP}$ =12.50 Hz $^{31}$P NMR P(v) $\delta$10.13 ppm,(d) P(III) $\delta$29.70 ppm (d), $^2J_{PP}$=5

Preparation of Ligand 1d [1-(N-4-cyanotetrafluorophenyl-diphenylphosphinimine -2-diphenylphosphino)ethane].

1,2-bisdiphenylphosphinoethane (0.956 g, 2.4 mmol) was placed in a 100 cm$^3$ round bottomed flask fitted with a dropping funnel and a magnetic stirrer and cooled to −78° C. with an acetone/CO$_2$ bath. Slow addition of tetrafluorobenzonitrile azide, N$_3$C$_6$F$_4$CN [Keana and Cai, op. cit.](0.57 g, 2.64 mmol) gave a pale yellow solution. On warming the reaction mixture to room temperature the solution turned to a bright sun yellow colour. The solvent was then removed under reduced pressure and the resultant residue was recrystallised twice from acetonitrile. (1.06 g, 80% yield) (mp=146°-156° C.).

$^{31}$P-($^1$H)(81 MHz) (CDCl$_3$):$\delta$−12.9 (d, 1P, J$_{PP}$ 47.5 Hz), −16.7 (d, 1P, J$_{PP}$47.5 Hz) ppm Preparation of Ligand 1e [1-(1,2-phenylene(diphenylphosphoranimine)-2-diphenylphosphino)benzene]

Into a Schlenk tube was placed: 5 g (20 mmol azide) of Amberlite anion exchange resin (chloride replaced by azide) [A. Hassner and M. Stern, *Angew. Chem. Int. Ed. Engl.* 25, (1986) 478], 1.00 g (5.85 mmol) of benzylbromide and enough CH$_2$Cl$_2$ to saturate the resin (20 cm$^3$). This mixture was stirred for eight hours at room temperature. The solution was then filtered under argon and the resin was washed with two 10 cm$^3$ portions of CH$_2$Cl$_2$. The CH$_2$Cl$_2$ solution containing the azide was then added dropwise to a CH$_2$Cl$_2$ solution (20 cm$^3$) of -1,2-bis(diphenylphosphino)-benzene (2.33 g, 5.22 mmol) at 0° C., The reaction mixture was allowed to warm slowly overnight and removal of the solvent in vacuo produced an oil. Dissolving the oil in a minimum of CH$_2$Cl$_2$ and the addition of 100 cm$^3$ of dry hexane produced an oil. The solvent was decanted from the oil and both fractions were analyzed by $^{31}$P NMR spectroscopy. The solvent fraction contained ligand 1e exclusively, but the oil contained a large variety of unknown phosphorus containing compounds. The solvent fraction was recrystallized from acetonitrile to yield approximately 1 g (30%) of pure 1e. M.P.=129°-131° C.

Analysis: C$_{37}$H$_{31}$P$_2$N. Calculated: C=80.57, H=5.66, N=2.54%. Found: C=80.19, H=5.68, N=2.98%. Calculated with 0.2 moles of acetonitrile: C=80.24, H=5.69, N=3.00%. I.R. (CH$_2$Cl$_2$ cast): 3050w, 2800w, 2120 (CH$_3$CN), 1585w, 1490w, 1480m, 1437s, 1280m br, 1182m, 1108s, 1026m, 998w, 724s br, 694vs, 548m, 530m. M.S.: M+−77=474 (100%). $^1$H NMR ($\delta$, CDCl$_3$, TMS) 7.8-6.9 ppm, Ar, 29H; 4.5 ppm, d, $^3J_{HP}$=16.97 Hz; (1.97 ppm CH$_3$CN). $^{31}$P NMR ($\delta$, CDCl$_3$, H$_3$PO$_4$) 10.3 ppm, d, $^3J_{pp}$=1.5.0 Hz; −13.9 ppm, d, $^3J_{pp}$=15.5 Hz. $^{13}$C NMR ($\delta$, CDCl$_3$, TMS) 138-125 ppm, Ar; 49.75 ppm, s.

Preparation of the preformed catalysis precursor compound type III

The compound

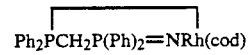

was prepared as described by K. V. Katti and R. G. Cavell *Organometallics*, (1988) 7,2236

Preparation of complexes Type I or II [{Rh(cod)-(ligand)}+PF$_6^-$]

General Method

The relevant ligand (1a, 1b or 1h) (0-8 mmol) was added to a mixture of [Rh(cod)Cl]$_2$ (0.2 g, 0.4 mmol) and KPF$_6$ (0.2 g, 1.0 mmol) in dichloromethane (30 cm$^3$) and water (20 cm$^3$). The mixture was stirred vigorously at room temperature for up to 2 h. The dichloromethane layer was then removed and washed with water to remove excess KPF$_6$. The dichloromethane layer was decanted once more and the volume reduced to about 5 cm$^3$ under reduced pressure. Addition of hexane to the solution precipitated the complexes as microcrystalline orange-brown powders, which were filtered and dried in vacuo.

Complexes of the Type I (i) {Rh(cod)(Ph$_2$PCH-(Me)P(Ph)$_2$=NC$_6$F$_4$CN)}+PF$_6^-$ Reaction of the ligand (Ph$_2$PCH(Me)P(Ph$_2$)=NC$_6$F$_4$CN), (1a), (0.46 g, 0.8 mmol) gave {Rh(cod)(Ph$_2$PCH-(Me)P(Ph)$_2$=NC$_6$F$_4$CN)}+PF$_6^-$ as a fine orange microcrystalline powder, (0.690 g, 93%): m.p. 168°–180° C. decomp.

Anal. Calcd for $C_{41}H_{34}F_{10}N_2P_3Rh$: C, 52.3; H, 3.8; N, 3.0. Found: C, 51.7; H, 3.9; N, 2.8%. $^1H$ NMR $(CD_2Cl_2)$: δ7.1–8.3 (m, 20H, Phenyl), 5.3 (m.br, 1H, cod olefinic), 4.4 (m.br, 1H, cod olefinic) 3.9 (ddq, 1H, $^3J(HH)$ 7.2, $^2J(HP^v)$ 12.2, $^2J(HP^{III})$ 22.2), 3.3 (m.br, 2H, cod olefinic), 1.7–2.7 (m, 8H, cod alkyl), 1.35 (ddd, 3H, $^3J(HH)$ 7.2, $^3J(HP^v)$ 10.4, $^3J(HP^{III})$ 18.0). $^{31}P$ NMR $(CD_2Cl_2)$: δ53.4 (d, 1P, $^2J(PP)$ 41.8), 31.92 (dd, 1P, $^2J(PP)$, 41.8, $^1J(PRh)$ 152.7), −144.3 (Sep, 1P, $^{11}J(PF)$ 710.8). MS (FAB): (100%); 796.4, [M]+.

(ii)$[Rh(cod)(Ph_2PC_6H_4P(Ph)_2=NC_6F_4CN)]^+PF_6^-$ Reaction with the ligand $Ph_2PC_6H_4P(Ph)_2=NC_6F_4CN$ (1b) (0.507 g, 0.8 mmol) gave $[Rh(cod)(Ph_2PC_6H_4P(Ph)_2=NC_6F_4CN)]^+PF_6^-$ as a fine yellow powder (0.775 g, 98%) mp 250° C. decomp.

Anal. Calcd for $C_{45}H_{36}F_{10}N_2P_2Rh+CH_2Cl_2$: C, 51.0; H, 3.6; N, 2.7. Found: C, 51.3; H, 3.5; N, 2.6%. $^1H$ NMR $(CD_2Cl_2)$ δ7.8 (m, 4H, aromatic), 7.4 (m, 20H, phenyl), 4.8 (s.br, 2H, olefinic cod), 3.2 (s.br, 2H, olefinic cod), 2.1 (m, 8H, alkyl cod). $^{31}P$ NMR $(CD_2Cl_2)$. δ30.6 (d, 1P, $^3J(PP)$ 25.2), 19.3 (dd, 1P, $^3J(PP)$ 25.2, $^1J(PRh)$ 154.2), −144 (Sept, 1P, $^1(PF)$ 711.2). MS (FAB); (100%) 845 [M+.

Complexes of the Type II (iii)$[Rh(cod)(Ph_2P-N=C(H)Ph)_2]^+PF_6^-$ Reaction with the ligand $Ph_2P-N=C(H)Ph$, (1h), (0.46 g, 1.6 mmol) gave $[Rh(cod)(Ph_2P-N=C(H)Ph)_2]^+PF_6^-$ as a fine orange-brown powder (0.49 g, 60%). mp 154°–156° C. decomp.

Anal. Calcd for $C_{46}H_{44}F_6N_2P_3Rh+CH_2Cl_2$: C, 55.3; H, 4.5; N, 2.7. Found: C, 55.2; H, 4.6; N, 2.7%. $^1H$ NMR $(CD_2Cl_2)$ δ5 8.0 (d, 2H, $^2J(PH)$ 29.6, N=CH), 7.2–7.7 (m, 30H, phenyl), 4.9 (s,br, 4H, olefinic cod), 2.45 (m, 8H, alkyl cod). $^{31}P$ NMR $(CD_2Cl_2)$ δ71.54 (d, 2P, $^1J(PRh)$ 158.8), −144.2 (Sept, 1P, 1P, $^1J(PF)$ 710.5). MS (FAB): (2.2%) 789 [M]+, (32%) 290 $[Ph_2PNCHPh]^+$.

Assembly and operation of the catalytic system.

General method.

One of methods A or B was used:

(A) The pro-prepared rhodium containing catalyst precursor (0.08 mmol) was dissolved in the relevant solvent, either dichloromethane or ethanol:benzene (1:1) (10 cm³) and placed in a 50 cm³ round-bottomed Schlenk flask, fitted with a septum cap and a magnetic stirrer bead, under an argon atmosphere.

(B) In-situ formation of catalyst precursors—$[Rh(cod)Cl]_2$ or a previously noted rhodium diolefin chlorine rhodium containing source (0.02 g 0.04 mmol) and the relevant phosphoraniminatophosphine ligand (0.08 mmol) were dissolved in the relevant solvent, (10 cm³) and placed in a 50 cm³ round-bottomed Schlenk flask fitted with a septum cap and a magnetic stirrer bead, under an argon atmosphere.

For both methods (A) and (B), an identical hydrogenation experimental procedure was followed. In both cases if an amine promoter component was to be employed in the experiment, the desired quantity of the amine was added to the catalyst solution after the initial preparation stage.

For hydrogenation efficacy tests, the Schlenk flask containing the catalytic solution prepared as described above was connected to a standard hydrogenation apparatus. The hydrogenation apparatus consisted of a 'leak free' glass line equipped with a manometer, gas burette and reservoir, and connected to a hydrogen supply and vacuum line. The Schlenk flask containing the catalytic solution was then evacuated and purged with hydrogen gas. This filling and purging process was repeated and on the third repeat the burette was also filled with hydrogen gas to displace the indicator solution into the reservoir. The level of indicator solution in the reservoir was brought slightly above the level of the indicator solution in the burette. The catalytic solution was then stirred magnetically under the hydrogen atmosphere (slight excess over 1 ambient atmosphere being slightly greater than the normal ca. 700 mm Hg atmospheric pressure which prevails in Edmonton, Canada) for fifteen minutes. The hydrogenatable reactant such as has previously been noted (0.01 mol) was then added to the catalytic solution via a syringe through the septum cap. The reservoir bulb was then adjusted again to maintain the internal pressure of the apparatus to a slight excess over the external atmospheric pressure. This positive pressure was maintained throughout the reaction time by frequent adjustment of the reservoir bulb. Hydrogen uptake was monitored in the graduated burette from the moment the hydrogenatable reactant was added to the system. The reaction was stopped when no further uptake of hydrogen could be observed. The reaction mixture containing the hydrogenation products was analyzed using a Shimadzu GC-14A gas chromatograph (G.C.) equipped with a capillary column (FFAP) (polyethylene glycol-acid modified) and a flame ionization detector (F.I.D). detector. The product identities were determined using commercially obtained compounds as standards. The hydrogenatable reactants were distilled under an argon atmosphere and passed through an alumina column immediately prior to use to remove peroxides. All experimental manipulations were performed under an atmosphere of dry argon. All solvents were dried using standard methods and distilled under an argon atmosphere prior to use. The known rhodium catalyst precursors $[Rh(cod)(PPh_3)_2]^+PF_6^-$ and $[Rh(cod)(dppb)]^+PF_6^-$, where cod=1,5 cyclooctadiene and dppb=1,4 bisdiphenylphosphinobutane, were prepared according to the procedure by Schrock and Osborn [*J. Am. Chem. Soc.* 98 (1976) 2134]. $[RhCl(PPh_3)_3]$ was obtained from commercial sources.

EXAMPLES

Example 1

Following general method (A), the catalyst precursor (0.0754 g, 0.08 mmol) having the formula $[Rh(cod)Ph_2PCH(Me)P(Ph)_2=NC_6F_4-(p)-CN]^+PF_6^-$ (type A) and a solvent (10 cm³), ethanol/benzene in a 1:1 ratio were placed in a Schlenk flask as previously describe. The addition of hex-1-ene (2 cm³, 16 mmol) to the flask under hydrogenation conditions gave a hydrogen uptake corresponding to a hydrogenation rate of 9.5 moles of hydrogen per mole of rhodium per hour (mol(-mol Rh)$^{-1 -1}$). Gas chromatographic (G.C.) analysis of the final reaction mixture showed hexane to be the sole product.

Example 2

Following the general method (A), the catalyst precursor (0.0754 g, 0.08 mmol) having the formula $[Rh(cod)Ph_2PCH(Me)P(Ph)_2=NC_6F_4-(p)-CN]^{+PF_6^-}$ (type A) and dichloromethane solvent ($^{10}$ cm³) were placed in a Schlenk flask as previously described. The additions of hex-1-ene (2 cm$^3$, 16 mmol) to the flask under hydrogenation conditions gave a hydrogen uptake corresponding to a hydrogenation rate of 8.0 moles of hydrogen per mole of rhodium per hour (mol(mol Rh)$^{-1}$ h$^{-1}$). G.C. analysis of the final reaction mixture showed hexane to be the sole product.

Example 3

Following the general method (B), (0.02 g, 0.04 mmol) of the rhodium compound [Rh(cod)Cl]$_2$ and the phosphoriminatophosphine ligand having the formula Ph$_2$PCH(Me)P(Ph)$_2$=NC$_6$F$_4$-(p)-CN (0.0469 g, 0.08 mmol) (Ligand 1a) and a promoter (0.2 cm$^3$, 1.4 mmol) triethylamine were placed in a Schlenk flask as previously described with a solvent, (10 cm$^3$) ethanol/benzene in a 1:1 ratio. The addition of hex-1-ene (2 cm$^3$, 16 mmol) under hydrogenation conditions gave a hydrogen uptake corresponding to a hydrogenation rate of 60.5 moles of hydrogen per mole of rhodium per hour (mol(mol Rh)$^{-1}$ h$^{-1}$). G.C. analysis of the final reaction mixture showed hexane as the sole product. This experiment demonstrates the combination of the precursor reagents to prepare the catalyst mixture in situ gives higher catalytic activity than introduction of separately prepared catalyst precursors.

Example 4

Following the general method (A), the catalyst precursor (0.0792 g, 0.08 mmol) having the formula [Rh(cod)Ph$_2$PC$_6$H$_4$P(Ph)$_2$=NC$_6$F$_4$-(p)-CN]$^+$PF$_6^-$ (type A), a promoter (0.2 cm$^3$, 1.4 mmol) triethylamine and a solvent, (10 cm$^3$) ethanol/benzene in a 1:1 ratio, were placed in a Schlenk flask as previously described. The addition of hex-1-ene (2 cm$^3$, 16 mmol) to the flask under hydrogenation conditions gave no hydrogen uptake and hence no hydrogenation had occurred. G.C. analysis of the mixture showed unreacted hex-1-ene.

Example 5

Following the general method (A) the catalyst precursor (0.0792 g, 0.08 mmol) having the formula [Rh(cod)Ph$_2$PC$_6$H$_4$P(Ph)$_2$=NC$_6$F$_4$-(p)-CN]$^+$PF$_6^-$ (type A), and dichloromethane solvent (10 cm$^3$) were placed in a Schlenk tube as previously described. The addition of hex-1-ene (2 cm$^3$, 16 mmol) to the flask under hydrogenation conditions gave a hydrogen uptake corresponding to a hydrogenation rate of 2.1 moles of hydrogen per mole of rhodium per hour, (mol(mol Rh)$^{-1}$ h$^{-1}$). G.C. analysis of the final reaction mixture showed hexane to be the only reaction product

Example 6

Following the general method (B), (0.02 g, 0.04 mmol) of the rhodium compound [Rh(cod)Cl]$_2$ and the phosphoriminatophosphine ligand having the formula Ph$_2$PC$_6$H$_4$P(Ph)$_2$=NC$_6$F$_4$-(p)-CN (0.0507 g, 0.08 mmol) (Ligand 1b) and a promoter triethylamine (0.2 cm$^3$, 1.4 mmol) were placed in a Schlenk flask as previously described with a solvent, (10 cm$^3$) ethanol/benzene in a 1:1 ratio. The addition of hex-1-ene (2 cm$^3$, 16 mmol) under hydrogenation conditions gave a hydrogen uptake corresponding to a hydrogenation rate of 25.5 moles hydrogen per mole rhodium per hour (mol(mol Rh)$^{-1}$ h$^{-1}$). G.C. analysis of the final reaction mixture showed hexane as the only reaction product. This example also demonstrates the greater catalytic activity of fresh in situ catalytic preparations of the current invention compared to pre-prepared catalyst precursors of the present invention.

Example 7

Following the general method (B), (0.02 g. 0.04 mmol) of the rhodium compound [Rh(cod)Cl]$_2$ and the phosphoriminatophosphine ligand having the formula Ph$_2$PCH$_2$P(Ph)$_2$=NC$_6$H$_3$(NO$_2$)$_2$ (0.0454 g, 0.08 mmol) (ligand 1c) and a promoter triethylamine (0.2 cm$^3$, 1.4 mmol) were placed in a Schlenk flask as previously described with a solvent, (10 cm$^3$) ethanol/benzene in a 1:1 ratio. The addition of hex-1-ene (2 cm$^3$, 16 mmol) under hydrogenation conditions gave a hydrogen uptake corresponding to a hydrogenation rate of 14.5 moles of hydrogen per mole rhodium per hour. G.C. analysis of the final reaction mixture showed hexane as the only reaction product.

Example 8

Following the general method (B), (0.02 g, 0.04 mmol) of the rhodium compound [Rh(cod)Cl]$_2$ and the phosphoriminatophosphine ligand having the formula Ph$_2$PCH$_2$CH$_2$P(Ph)$_2$=NC$_6$F$_4$-(p)-CN (0.0469, 0.08 mmol) (Ligand 1d) and a promoter triethylamine (0.2 cm$^3$, 1.4 mmol) were placed in a Schlenk flask as previously described with a solvent, (10 cm$^3$) ethanol/benzene in a 1:1 ratio. The addition of hex-1-ene (2 cm$^3$, 16 mmol) to the reaction under hydrogenation conditions gave a hydrogen uptake corresponding to a hydrogenation rate of 27.5 moles of hydrogen per mole rhodium per hour (mol(mol Rh)$^{-1}$ h$^{-1}$). G.C. analysis of the final reaction mixture showed hexane as the only product.

Example 9

Following the general method (A) the separately prepared catalyst precursor (0.0487 g, 0.08 mmol) having the formula

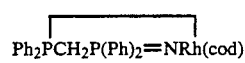

a promoter (0.2 cm$^3$, 1.4 mmol) triethylamine and solvent, (10 cm$^3$) ethanol/benzene in a 1:1 ratio, were placed in a Schlenk flask as previously described. The addition of hex-1-ene (2 cm$^3$, 16 mmol) to the reaction under hydrogenation conditions gave a hydrogen uptake corresponding to a hydrogenation rate of 88.0 moles of hydrogen per mole of rhodium per hour. G.C. analysis of the final reaction mixture showed hexane as the only reaction product. It is noted that rates of hydrogenation in this example were inconsistent and non-reproducible, indicating that some instability or decomposition of the catalyst or catalyst precursor compound may take pie with time which results in a loss of activity.

Example 10

Following the general method (B), (0.02 g, 0.04 mmol) of the rhodium compound [Rh(cod)Cl]$_2$ and the phosphoriminatophosphine ligand having the formula Ph$_2$PC$_6$H$_4$P(Ph)$_2$=NCH$_2$Ph (0.0391 g, 0.08 mmol) (Ligand 1e) and a promoter triethylamine (0.2 cm$^3$, 1.4 mmol) were placed in a Schlenk flask as previously described with a solvent, (10 cm$^3$) ethanol/benzene in a 1:1 ratio. The addition of hex-1-ene to the reaction conditions under hydrogenation conditions gave a hydrogen uptake corresponding to a hydrogenation rate of 11.3 moles of hydrogen per mole rhodium per hour, G.C. analysis of the final reaction mixture showed hexane to be the only reaction product.

Example 11

Following the general method (B), (0.02 g, 0.04 mmol) of the rhodium compound [Rh(cod)Cl]$_2$ and the phosphoriminatophosphine ligand having the formula Ph$_2$PCH$_2$P(Ph)$_2$=NSiMe$_3$ (0.0378 g, 0.08 mmol) (Ligand 1f) and a promoter triethylamine (0.2 cm$^3$, 1.4 mmol) were placed in a Schlenk flask as previously described with a solvent, (10 cm$^3$ ethanol/benzene in a 1:1 ratio. The addition of hex-1-ene to the reaction under hydrogenation conditions gave a hydrogen uptake corresponding to a hydrogenation rate of 275.0 moles of hydrogen per mole rhodium per hour. G.C. analysis of the final reaction mixture showed hexane as the only reaction product. This example shows that a fresh in situ preparation of the catalyst precursor with the presumed formula

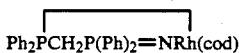

Ph$_2$PCH$_2$P(Ph)$_2$=NRh(cod)

from the reagents gives significantly higher catalytic activity, relative to that in example 9 wherein the presumed catalytic precursor compound was prepared separately before use in the catalytic system.

Example 12

Following the general method (B), (0.02 g, 0.04 mmol) of the rhodium compound [Rh(cod)Cl]$_2$ and the phosphoriminatophosphine ligand having the formula Ph$_2$CH$_2$CH$_2$P(Ph)$_2$=NSiMe$_3$ (0.0389 g, 0.08 mmol) (Ligand 1g) prepared according to the method of Katti et al., *Inorg. Chem.* 29 (1990) 808, and a promoter triethylamine (0.2 cm$^3$, 1.4 mmol) were placed in a Schlenk flask as previously described with a solvent, (10 cm$^3$) ethanol/benzene in a 1:1 ratio. The addition of hex-1-ene to the flask under hydrogenation conditions gave a hydrogen uptake corresponding to a hydrogenation rate of 54.5 moles of hydrogen per mole of rhodium per hour (mol(mol Rh)$^{-1}$ h$^{-1}$). G.C. analysis of the final reaction mixture showed hexane as the only reaction product. This example shows that increase in carbon backbone length from —CH$_2$— to —CH$_2$CH$_2$— to give a six-membered rhodium-ligand chelation compound gives lower reactivity than was shown in example 11 wherein a shorter, —CH$_2$— carbon backbone was used.

Example 13

Following the general method (A), the catalyst precursor (0.0747 g, 0.08 mmol) having the formula [Rh(cod)(Ph$_2$PN=C(H)Ph)$_2$]+PF$_6$− (type B), a promoter (0.2 cm$^3$, 1.4 mmol) triethylamine and a solvent, (10 cm$^3$) ethanol/benzene in a 1:1 ratio, were placed in a Schlenk flask as previously described. The addition of hex-1-ene (2 cm$^3$, 16 mmol) to the reaction under hydrogenation conditions gave a hydrogen uptake corresponding to a hydrogenation rate of 93.0 moles of hydrogen per mole rhodium per hour. G.C. analysis of the final reaction mixture showed hexane as the only reaction product. This example demonstrates the use of the N-diphenylphosphinobenzalimine ligand (Ph$_2$P-N=C(H)Ph) (Ligand 1h) in a rhodium catalyst precursor as previously described. It is noted that the catalytic activity of the catalyst precursor in this example is greater than other catalyst precursors in the present invention having the formula [Rh(diolefin)-(ligand)]+PF$_6$−. This is apparently due to the greater solubility (in the selected solvents) of the catalyst precursor in this example.

Example 14

Following the general method (B), (0.02 g, 0.04 mmol) of the rhodium compound [Rh(cod)Cl]$_2$ and the standard phosphine ligand having the formula PPh$_3$ (0.052 g, 0.02 mmol) with a solvent (10 cm$^3$) ethanol were placed in a Schlenk flask as previously described. The addition of hex-1-ene to the flask under catalytic conditions gave a hydrogen uptake corresponding to a hydrogenation rate of 62.5 moles of hydrogen per mole rhodium per hour (mol (mol Rh)$^{-1}$ h$^{-1}$). G.C. analysis of the final reaction mixture showed hexane as the sole reaction product. This example illustrates the use of a known rhodium-phosphine catalytic system under identical conditions to that of the present invention.

Example 15

Following the general method (A), the catalyst precursor (0.0704 g, 0.08 mmol) having the formula [Rh(cod)(PPh$_3$)$_2$]+PF$_6$− and a solvent, (10 cm$^3$) dichloromethane, were placed in a Schlenk flask as previously described. The addition of hex-1-ene to the flask under catalytic conditions have a hydrogen uptake corresponding to a hydrogenation rate of 236.0 moles of hydrogen per mole rhodium per hour (mol(mol Rh)$^{-1}$ h$^{-1}$). G.C. analysis of the final reaction mixture showed hexane as the only product. This example also demonstrates the performance of a known hydrogenation catalyst precursor under identical reaction conditions to those of the present invention.

Example 16

Following the general method (B), (0.02 g, 0.04 mmol) of the rhodium compound [Rh(cod)Cl]$_2$ and the phosphoriminatophosphine ligand having the formula Ph$_2$PCH$_2$P(Ph)$_2$=NSiMe$_3$ (0.0283 g, 0.06 mmol) (Ligand 1f) and a promoter triethylamine (0.2 cm$^3$, 1.4 mmol) in a solvent (10 cm$^3$) ethanol, were placed in a Schlenk flask as previously described. The addition of hex-1-ene to the flask under catalytic conditions gave a hydrogen uptake corresponding to a hydrogenation rate of 428.0 moles of hydrogen per mole rhodium per hour. G.C. analysis of the final reaction mixture showed hexane as the only reaction product. This example demonstrates a rhodium to ligand ratio of 4:3 (1:0.75) and the use of ethanol as the reaction solvent and is to be compared to example 11 where a rhodium to ligand ratio of 1 to 1 was employed and ethanol/benzene in a 1 to 1 ratio used as the reaction solvent.

Example 17

Following the general method (B), (0.02 g, 0.04 mmol) of the rhodium compound [Rh(cod)Cl]$_2$ and the phosphoriminatophosphine ligand having the formula Ph$_2$PCH$_2$P(Ph)$_2$=NSiMe$_3$ (0.0378 g, 0.08 mmol) (Ligand 1f) and a promoter triethylamine (0.2 cm$^3$, 1.4 mmol) in a solvent, (10 cm$^3$) ethanol, were placed in a Schlenk flask as previously described. The addition of hex-1-ene to the flask under catalytic conditions gave a hydrogen uptake corresponding to a hydrogenation rate of 499.0 moles of hydrogen per mole rhodium per hour. G.C. analysis of the reaction products showed hexane as the only reaction product. This example demonstrates the behavior of a system with a rhodium to ligand ratio of 1 to 1 and the use of ethanol as the reaction solvent and is to be compared to example 16.

Example 18

Following the general method (B), (0.02 g, 0.04 mmol) of the rhodium compound [Rh(cod)Cl]$_2$ and the phosphoriminatophosphine ligand having the formula Ph$_2$PCH$_2$P(Ph)$_2$=NSiMe$_3$ (0.0472 g, 0.1 mmol) (Ligand 1f) and a promoter triethylamine (0.2 cm$^3$, 1.4 mmol) in a solvent, (10 cm$^3$) ethanol, were placed in a Schlenk flask as previously described. The addition of hex-1-ene to the flask under catalytic conditions gave a hydrogen uptake corresponding to a hydrogenation rate of 430.0 moles of hydrogen per mole rhodium per hour. G.C. analysis of the reaction products showed hexane as the only reaction product. This example demonstrates the catalytic activity of this system using a rhodium to ligand ratio of 4 to 5 (1:1.25) compared to the ratios used in the previous examples 16 and 17.

Example 19

Following the general method (B), (0.02 g, 0.04 mmol) of the rhodium compound [Rh(cod)Cl]$_2$ and the phosphoriminatophosphine ligand having the formula Ph$_2$PCH$_2$P(Ph)$_2$=NSiMe$_3$ (0.0566 g, 0.12 mmol) (Ligand 1f) and a promoter triethylamine (0.2 cm$^3$, 1.4 mmol) in a solvent (10 cm$^3$) ethanol, were placed in a Schlenk flask as previously described. The addition of hex-1-ene to the flask under catalytic conditions gave a hydrogen uptake corresponding to a hydrogenation rate of less than one mole of hydrogen per mole of rhodium per hour. The G.C. analysis of the final reaction mixture showed hexane to be the only reaction product. This example demonstrates the effect on catalytic activity in this system when a rhodium to ligand ratio of 1 to 3 is employed and is to be compared to the results of examples 16, 17 and 18.

Example 20

Following the general method (B), (0.02 g, 0.04 mmol) of the rhodium compound [Rh(cod)Cl]$_2$ and the phosphoriminatophosphine ligand having the formula Ph$_2$PCH$_2$P(Ph)$_2$=NSiMe$_3$ (0.0378 g, 0.08 mmol). (Ligand 1f) and the trimethylamine promoter (0.2 cm$^3$ 1.4 mmol) and benzene solvent (10 cm$^3$) were placed in a Schlenk flask as previously described. The addition of hex-1-ene to the flask under catalytic conditions gave a hydrogen uptake of less than one mole of hydrogen per mole rhodium per hour. G.C. analysis of the final reaction mixture showed hexane as the only reaction product. This example shows that catalytic hydrogenation in this system is suppressed by the use of benzene as a reaction solvent.

Example 21

Following the general method (B), (0.02 g, 0.04 mmol) of the rhodium compound [Rh(cod)Cl]$_2$ and the phosphoriminatophosphine ligand having the formula Ph$_2$PCH$_2$P(Ph)$_2$=NSiMe$_3$ (0.0378 g, 0.08 mmol), (Ligand 1f), and a promoter triethylamine (0.2 cm$^3$, 1.4 mmol), in a solvent, (10 cm$^3$) dichloromethane, were placed in a Schlenk flask as previously described. The addition of hex-1-ene (2 cm$^3$, 16 mmol) to the flask under catalytic conditions gave no hydrogen uptake and hence no reaction. G.C. analysis of the mixture showed only unreacted hex-1-ene. This example shows that in this system, dichloromethane is not a preferred solvent.

Example 22

Following the general method (B), (0.02 g, 0.04 mmol) of the rhodium compound [Rh(cod)Cl]$_2$ and the phosphoriminatophosphine ligand having the formula Ph$_2$PCH$_2$P(Ph)$_2$=NSiMe$_3$ (0.0378 g, 0.08 mmol) (Ligand 1f), and a promoter diethylamine (0.15 cm$^3$, 1.4 mmol) in ethanol solvent (10 cm$^3$), were placed in a Schlenk flask as previously described. The addition of hex-1-ene (2 cm$^3$, 16 mmol) to the flask under catalytic conditions gave a hydrogen uptake corresponding to a hydrogenation rate of 285.0 moles of hydrogen per mole rhodium per hour. G.C. analysis of the final reaction mixture showed hexane as the only reaction product. This example demonstrates the use of diethylamine as a promoter showing it to be less effective than triethylamine under identical conditions to those used in example 17.

Example 23

Following the general method (B), (0.02 g, 0.04 mmol) of the rhodium compound [Rh(cod)Cl]$_2$ and the phosphoriminatophosphine ligand having the formula Ph$_2$PCH$_2$P(Ph)$_2$=NSiMe$_3$ (0.0378 g, 0.08 mmol) (Ligand 1f) , and a promoter morpholine (0.12 cm$^3$, 1.4 mmol) in ethanol solvent (10 cm$^3$), were placed in a Schlenk flask as previously described. The addition of hex-1-ene (2 cm$^3$, 16 mmol) to the flask under catalytic conditions gave a hydrogen uptake corresponding to a hydrogenation rate of 6.0 moles of hydrogen per mole rhodium per hour. G.C. analysis of the final mixture showed hexane as the only reaction product. This example demonstrates that morpholine is less effective as a promoter than triethylamine under identical conditions to those used in example 17.

Example 24

Following the general method (B), (0.02 g, 0.04 mmol) of the rhodium compound [Rh(cod)Cl]$_2$ and the phosphoriminatophosphine ligand having the formula Ph$_2$PCH$_2$P(Ph)$_2$=NSiMe$_3$ (0.0378 g, 0.08 mmol) (Ligand 1f), and a promoter pyridine (0.11 cm$^3$, 1.4 mmol) in ethanol solvent (10 cm$^3$), were placed in a Schlenk flask as previously described. The addition of hex-1-ene (2 cm$^3$, 16 mmol) to the flask under catalytic conditions gave an initial hydrogen uptake corresponding to a hydrogenation rate of 23.0 moles of hydrogen per mole rhodium per hour (mol (mol Rh)$^{-1}$ h$^{-1}$) after which the catalyst decomposed to give metallic rhodium and the reaction was aborted. This example demonstrates that pyridine is not effective as a reaction promoter.

Example 25

Following the general method (B), (0.02 g, 0.04 mmol) of the rhodium compound [Rh(cod)Cl]$_2$and the phosphoriminatophosphine ligand having the formula Ph$_2$PCH$_2$P(Ph)$_2$=NSiMe$_3$ (0.0378 g, 0.08 mmol) (Ligand 1f) in a solvent, (10 cm$^3$) ethanol/benzene in a 1:1 ratio, were placed in a Schlenk flask as previously described. Addition of hex-1-ene (2 cm$^3$, 16 mmol) to the flask under catalytic conditions showed no hydrogen uptake and no reaction. This example demonstrates that no catalysis takes place in the presently described catalyst system without the presence of an amine promoter.

Example 26

Following the general method (B), (0.02 g, 0.04 mmol) of the rhodium compound [Rh(cod)Cl]$_2$ and the phosphoriminatophosphine ligand having the formula Ph$_2$PCH$_2$P(Ph)$_2$=NSiMe$_3$ (0.0378 g, 0.08 mmol) (Ligand 1f), the trimethylamine promoter (0.2 cm$^3$, 1.4 mmol) and ethanol solvent (10 cm$^3$), were placed in a Schlenk flask as previously described. The addition of four batches of hex-1-ene (2 cm$^3$, 16 mmol) to the reaction mixture under catalytic conditions, consecutive batches being added when seventy five percent of the previous batch had been consumed (indicated by hydrogen uptake), gave rates of hydrogen uptakes corresponding to hydrogenation rates of 430, 390, 275, and 230 moles hydrogen per mole rhodium per hour (mol(-mol Rh)$^{-1}$ h$^{-1}$), respectively. After all four batches had been hydrogenated the G.C. analysis of the final reaction mixture showed hexane as the only reaction product. This example demonstrates the use of the presently described catalytic system in a repetitive sequence of batch experiments.

Example 27

Following general method (A), the catalyst precursor (0.0739 g, 0.08 mmol) having the formula [RhCl(PPh$_3$)$_3$] and a solvent, (10 cm$^3$) ethanol/benzene in a 1:1 ratio, were placed in a Schlenk flask as previously described. The addition of hex-1-ene (2 cm$^3$, 16 mmol) to the flask under catalytic conditions gave a hydrogen uptake co, responding to a hydrogenation rate of 380.0 moles of hydrogen per mole rhodium per hour. G.C. analysis of the final reaction mixture showed hexane as the only reaction product. This example shows the behaviour of the hydrogenation catalyst precursor known as "Wilkinson's Catalyst" [Osborn et. al.,op. cit.] under identical conditions to the present invention.

Example 28

Following the general method (A), the catalyst precursor (0.061, 0.08 mmol) having the formula [Rh(cod)dppb]$^+$PF$_6^-$ and a dichloromethane solvent (10 cm$^3$), were placed in a Schlenk flask as previously described. The addition of hex-1-ene (2 cm$^3$, 16 mmol) to the flask under catalytic conditions gave a hydrogen uptake corresponding to a hydrogenation rate of 370.0 moles of hydrogen per mole rhodium per hour. G.C analysis of the final reaction mixture showed hexane as the only product. This example shows the performance of the catalyst system described by Halpern and Landis [op. cit.] under conditions identical to those used in the present invention.

Example 29

Following the general method (B), (0.02 g, 0.04 mmol) of the rhodium compound [Rh(cod)Cl]$_2$ the phosphoriminatophosphine ligand having the formula Ph$_2$PCH$_2$P(Ph)$_2$=NSiMe$_3$(0.0378 g, 0.08 mmol) (Ligand 1f) and a promoter triethylamine (0.2 cm$^3$, 1.4 mmol), in ethanol solvent (10 cm$^3$), were placed in a Schlenk flask as previously described. The addition of cyclohexene (1.6 cm$^3$, 16 mmol) to the flask under conditions gave a hydrogen uptake corresponding to a hydrogenation rate of 660.0 moles of hydrogen per mole rhodium per hour. G.C. analysis of the final reaction mixture showed cyclohexane as the sole reaction product. This example shows the use of the described catalytic system of the present invention in the homogeneous catalytic hydrogenation of cyclohexene.

Example 30

Following the general method (A), the catalyst precursor (0.0704 g, 0.08 mmol) having the formula [Rh(cod)(PPh$_3$)$_2$]$^+$PF$_6^-$ and dichloromethane solvent (10 cm$^3$), were placed in a Schlenk flask as previously described. The addition of cyclohexene to the catalytic solution gave a hydrogen uptake corresponding to a hydrogenation rate of 238.0 moles of hydrogen per mole rhodium per hour. G.C. analysis of the final reaction mixture showed cyclohexane (1.6 cm$^3$, 16 mmol) as the only reaction product. This example shows the use of the known catalyst precursor described by Crabtree el. al. [op.cit.] for the hydrogenation of cyclohexene under identical conditions to those used for the present invention and in comparison to the result of example

Example 31

Following general method (A), the catalyst precursor (0.0739 g, 0.08 mmol) having formula [RhCl(PPh$_3$)$_3$] and a solvent, ethanol/benzene (10 cm$^3$) in a ratio of 1:1, were placed in a Schlenk flask as has previously been described. Addition of cyclohexene (1.6 cm$^3$, 16 mmol) to the flask under catalytic conditions show a hydrogen uptake corresponding to a hydrogenation rate at 356.0 moles of hydrogen per mole of rhodium per hour. G.C. analysis of the final reaction mixture showed cyclohexane as the only reaction product. This is another example of the use of the known catalyst precursor, "Wilkinson's Catalyst", in the hydrogenation of cyclohexene under conditions identical to those of the present invention.

Example 32

Following general method (A), the catalyst precursor (0.061 g, 0.08 mmol) having the formula [Rh(cod)(dppb)]$^+$PF$_6^-$ and dichloromethane solvent (10 cm$^3$), were placed in a Schlenk flask as previously described. The addition of cyclohexene (1.6 cm$^3$, 16 mmol) to the flask under catalytic conditions gave a hydrogen uptake corresponding to a hydrogenation rate of 499.0 moles of hydrogen per mole rhodium per hour. G.C. analysis of the final reaction mixture showed cyclohexene as the only reaction product. This serves as another example of the behavior of the known catalyst precursor described by Halpern and Landis [op. cit.]in the hydrogenation of cyclohexene under identical conditions to those used in the present invention.

Example 33

Following the general method (B), (0.02 g, 0.04 mmol) of the rhodium compound [Rh(cod)Cl]$_2$ the phosphoriminatophosphine ligand having the formula Ph$_2$PCH$_2$P(Ph)$_2$=NSiMe$_3$ (0.0378 g, 0.08 mmol) (Ligand 1r) and a promoter triethylamine (0.2 cm$^3$, 1.4 mmol) in ethanol solvent (10 cm$^3$),were placed in a Schlenk flask as previously described. The addition of styrene (1.8 cm$^3$, 16 mmol) to the flask under catalytic conditions gave a hydrogen uptake corresponding to a hydrogenation rate of 285.0 moles of hydrogen per mole rhodium per hour. G.C. analysis of the final reaction mixture showed ethylbenzene as the only reaction product.

Example 34

Following general method (A), the catalyst precursor (0.0739 g, 0.08 mmol) having the formula [RhCl(PPh$_3$)$_3$] and a solvent, ethanol/benzene (10 cm$^3$) in a 1:1 ratio, were placed in a Schlenk flask as previously described. Addition of styrene (1.8 cm$^3$, 16 mmol) to the flask under hydrogenation conditions gave a hydrogen uptake at 468.0 moles of hydrogen per mole of rhodium per hour. G.C. analysis of the final reaction mixture showed ethyl benzene as the sole reaction product. This example shows the use of the known catalyst precursor, "Wilkinson's Catalyst", in the hydrogenation of styrene, under conditions identical to those used in the present invention.

Example 35

Following method (A), the catalyst precursor (0.0704 g, 0.08 mmol) having the formula [Rh(cod)(PPh$_3$)$_2$]$^+$PF$_6^-$ and dichloromethane solvent (10 cm$^3$), were placed in a Schlenk flask as previously described. Addition of styrene (1.8 cm$^3$, 16 mmol) to the flask under catalytic conditions gave a hydrogen uptake corresponding to a hydrogenation rate of 17 moles of hydrogen per mole rhodium per hour. G.C. analysis of the final reaction mixture showed ethyl benzene as the only reaction product. The example shows the behavior of the known catalyst described by Crabtree et. al. [op. cit.] for the hydrogenation of styrene under identical conditions to those used in the present invention.

hex-1-ene. After 45 minutes the reactant composition was 92.6% hexane; 6.5% cis and trans hex-2-ene; 0.9% hex-1-ene. This example shows that some isomerisation of the reactant takes place in the hydrogenation of hex-1-ene with the described catalytic system. This example also illustrates a slowing of the reaction rate as cis and trans hex-2-ene are slower to hydrogenate than hex-1-ene.

The results of the above examples are summarized in Tables 1–4

Observations/Advantages

1) Rhodium(I) compounds with bidentate phosphoranimine ligands of the type R$_2$PQPR$_2$=NR in combination with a co-catalyst such as an alkyl amine are excellent catalysts for hydrogenation of olefins yielding hydrogenation products in quantitative yields.

2) Catalyst precursors of the type [Rh(diolefin)-(ligand)]$^+$PF$_6^-$ are moderately effective in the presence of a promoter.

3) "In-situ" catalyst preparations made by combining bifunctional phosphoraniminatophosphine ligands and the co-catalyst are the most preferred catalysts for catalytic hydrogenation.

4) "In-situ" catalyst preparations made by combining bifunctional phosphoraniminatophosphine ligands carrying a trimethylsilyl substituent on the imine nitrogen in combination with co-catalyst amine are the most preferred for homogeneous hydrogenation of hexene, cyclohexene and styrene as nonlimiting examples.

TABLE 1

The Hydrogenation of Hex-1-ene[a]

| Ex. No | Catalyst System | Solvent | Rate, (mol(molRh)$^{-1}$h$^{-1}$) |
|---|---|---|---|
| 1 | [Rh(cod)Ph$_2$PCH(Me)PPh$_2$=NC$_6$F$_4$CN]$^+$PF$_6^-$ | EtOH/benzene | 9.5 |
| 2 | [Rh(cod)Ph$_2$PCH(Me)PPh$_2$=NC$_6$F$_4$CN]$^+$PF$_6^-$ | CH$_2$Cl$_2$ | 8.0 |
| 3 | [Rh(cod)Cl]$_2$/Ph$_2$PCH(Me)PPh$_2$=NC$_6$F$_4$CN/NEt$_3$ | EtOH/benzene | 60.5 |
| 4 | [Rh(cod)Ph$_2$PC$_6$H$_4$PPh$_2$=NC$_6$F$_4$CN]$^+$PF$_6^-$/NEt$_3$ | EtOH/benzene | no reaction |
| 5 | [Rh(cod)Ph$_2$PC$_6$H$_4$PPh$_2$=NC$_6$F$_4$CN]$^+$PF$_6^-$ | CH$_2$Cl$_2$ | 2.1 |
| 6 | [Rh(cod)Cl]$_2$/Ph$_2$PC$_6$H$_4$PPh$_2$=NC$_6$F$_4$CN/NEt$_3$ | EtOH/benzene | 25.5 |
| 7 | [Rh(cod)Cl]$_2$/Ph$_2$CH$_2$PPh$_2$=NC$_6$H$_3$(NO$_2$)$_2$/NEt$_3$ | EtOH/benzene | 14.5 |
| 8 | [Rh(cod)Cl]$_2$/Ph$_2$P(CH$_2$)$_2$PPh$_2$=NC$_6$F$_4$CN/NEt$_3$ | EtOH/benzene | 27.5 |
| 9 | Ph$_2$PCH$_2$P(Ph)$_2$=NRh(cod)/NEt$_3$ | EtOH/benzene | 88.0 |
| 10 | [Rh(cod)Cl]$_2$/Ph$_2$PCH$_2$PPh$_2$=NCH$_2$Ph/NEt$_3$ | EtOH/benzene | 11.3 |
| 11 | [Rh(cod)Cl]$_2$/Ph$_2$PCH$_2$PPh$_2$=NSiMe$_3$/NEt$_3$ | EtOH/benzene | 275 |
| 12 | [Rh(cod)Cl]$_2$/Ph$_2$P(CH$_2$)$_2$PPh$_2$=NSiMe$_3$/NEt$_3$ | EtOH/benzene | 54.5 |
| 13 | [Rh(cod)(Ph(H)C=NPPh$_2$)$_2$]$^+$PF$_6^-$ | EtOH/benzene | 93.0 |
| 14 | [Rh(cod)Cl]$_2$ + 4PPh$_3$ | EtOH | 62.5 |
| 15 | [Rh(cod)(PPh$_3$)$_2$]$^+$PF$_6^-$ | CH$_2$Cl$_2$ | 236 |

[a]The general procedures applicable to all experiments are described above with particular details delineated in each example description given above.

Example 36

Following the general method (B), (0.02g, 0.04 mmol) of the rhodium compound [Rh(cod)Cl]$_2$ and the phosphoriminatophosphine ligand having the formula Ph$_2$PCH$_2$P(Ph)$_2$=NSiMe$_3$ (0.038 g, 0.08 mmol) (ligand 1f) and a promotor triethylamine (0.2 cm$^3$, 1.4 mmol) in ethanol solvent (10 cm$^3$), were placed in a Schlenk flask as previously described. The addition of hex-1-ene to the flask under catalytic conditions gave a hydrogen uptake corresponding to a hydrogenation rate of 500 moles of hydrogen per mole rhodium per hour. G.C. analysis of the reaction mixture showed a maximum of hex-1-ene isomerised to cis and trans hex-2-ene after 15 minutes reaction time, The reactant composition being 78.7% hexane; 18.2% cis and trans hex-2-ene; 3.1%

TABLE 2

Hydrogenation of Hex-1-ene.[a]

| Ex. No | Catalyst system (with additive)[b] | Solvent | Rate (mol(mol Rh)$^{-1}$h$^{-1}$) |
|---|---|---|---|
| 16 | [Rh(cod)Cl]$_2$/ 1.5 PCPNT/NEt$_3$ | EtOH | 428 |
| 17 | [Rh(cod)Cl]$_2$/ 2 PCPNT/NEt$_3$ | EtOH | 499 |
| 18 | [Rh(cod)Cl]$_2$/ 2.5 PCPNT/NEt$_3$ | EtOH | 430 |
| 19 | [Rh(cod)Cl]$_2$/ 3 PCPNT/NEt$_3$ | EtOH | <1 |
| 20 | [Rh(cod)Cl]$_2$/ 2 PCPNT/NEt$_3$ | benzene | <1 |
| 21 | [Rh(cod)Cl]$_2$/ 2 PCPNT/NEt$_3$ | CH$_2$Cl$_2$ | no reaction |

TABLE 2-continued

Hydrogenation of Hex-1-ene.[a]

| Ex. No | Catalyst system (with additive)[b] | Solvent | Rate (mol(mol Rh)$^{-1}$h$^{-1}$) |
|---|---|---|---|
| 22 | [Rh(cod)Cl]$_2$/ 2 PCPNT/NHEt$_2$ | EtOH | 285 |
| 23 | [Rh(cod)Cl]$_2$/ 2 PCPNT/morpholine | EtOH | 6 |
| 24 | [Rh(cod)Cl]$_2$/ 2 PCPNT/pyridine | EtOH | 23 |
| 25 | [Rh(cod)Cl]$_2$/ 2 PCPNT | EtOH/ benzene | no reaction |
| 26 | [Rh(cod)Cl]$_2$/ 2 PCPNT/NEt$_3$ | EtOH | Four batches of substrate 430,390,275,230 |
| 27 | [RhCl(PPh$_3$)$_3$] | EtOH/ benzene | 380 |
| 28 | [Rh(cod)dppb]$^+$PF$_6^-$ | CH$_2$Cl$_2$ | 570 |

[a]The general procedures applicable to all experiments are described above with particular details delineated in each example description given above.
[b]Amine additive to rhodium ratio 18:1 in all runs wherein an additive is employed.

TABLE 3

Hydrogenation of Cyclohexene[a]

| Ex. No | Catalyst system (additive)[b] | Solvent | Rate (mol(mol Rh)$^{-1}$h$^{-1}$) |
|---|---|---|---|
| 29 | [Rh(cod)Cl]$_2$/ 2 PCPNT/NEt$_3$ | EtOH | 660 |
| 30 | [Rh(cod)(PPh$_3$)$_2$]$^+$PF$_6^-$ | CH$_2$Cl$_2$ | 238 |
| 31 | [RhCl(PPh$_3$)$_3$] | EtOH/ benzene | 356 |
| 32 | [Rh(cod)dppb]$^+$PF$_6^-$ | CH$_2$Cl$_2$ | 499 |

[a]The general procedures applicable to all experiments are described above with particular details delineated in each example description given above.
[b]Amine additive to rhodium ratio 18:1 in all runs wherein an additive is employed.

TABLE 4

Hydrogenation of Styrene

| No | Catalyst system | Solvent | Rate (mol(mol Rh)$^{-1}$h$^{-1}$) |
|---|---|---|---|
| 33 | [Rh(cod)Cl]$_2$/ 2 PCPNT/NEt$_3$ | EtOH | 285 |
| 34 | [RhCl(PPh$_3$)$_3$] | EtOH/ benzene | 468 |
| 35 | [Rh(cod)(PPh$_3$)$_2$]$^+$PF$_6^-$ | CH$_2$Cl$_2$ | 17 |

PCPNT=Ph$_2$PCH$_2$P(Ph)$_2$=NSiMe$_3$ (ligand 1f); catalyst concentration, 8 × 10$^{-5}$ mol, substrate concentration approx 0.02 mol; Rate measured as fastest rate observed. Usually within the first minute of reaction. All reactions carried out at 23° C. and p(H$_2$) 1.1 atmospheres. In each case an induction time of 15 min was allowed under p(H$_2$) before addition of the substrate.

The entire disclosure of all applications, patents, and publications cited herein are hereby incorporated by reference.

The preceding examples can be repeated with similar success by substituting the generically or specifically described reactants and/or operating conditions of this invention for those used in the preceding examples.

From the foregoing description, one skilled in the art can easily ascertain the essential characteristics of this invention, and without departing from the spirit and scope thereof, can make various changes and modifications of the invention to adapt it to various usages and conditions.

We claim:

1. A process for hydrogenating a non-aromatic unsaturated hydrocarbon, comprising: reacting the hydrocarbon with a catalyst precursor which includes a source of a group VIIIB transition metal from the second and third rows of the periodic table and a heterobifunctional ligand constructs with a phosphine center and an imine nitrogen center, in the presence of hydrogen and a promoter selected from secondary or tertiary acyclic alkyl mines in a suitable solvent which solubilizes the hydrocarbon, catalyst precursor, the hydrogen, and the promoter.

2. The process of claim 1, wherein the catalyst precursor is selected from the general formulae I, B or III:

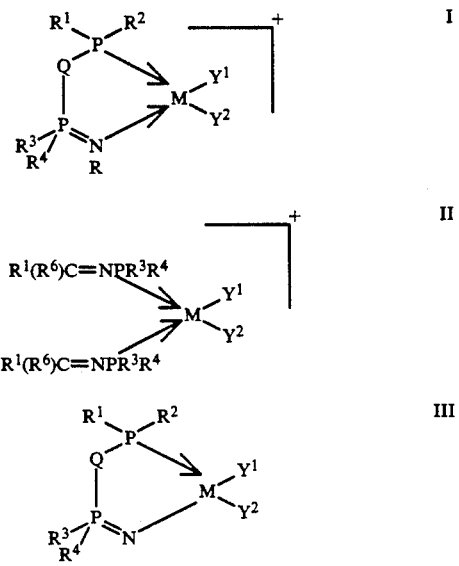

where R$^1$-R$^4$=same or different, substituted or unsubstituted, alkyl, aryl, alkoxide, aryloxide, amino, or thiol group;

Y$^1$y, Y$^2$=same or different, olefinic hydrocarbons;

Q=(CH$_2$)$_n$, wherein n=1-5, a benzene ring connected to the P atoms in the ortho positions, an olefin connected to the P atoms in the cis position, C(H)CH$_3$ or a substituted amine N(R$^7$);

R$^6$ =hydrogen or the substituents as defined for R$^1$-R$^5$ above;

R$^7$=substituted or unsubstituted aryl or alkyl;

M=Group VIIIB transition metal from the second or third row of the periodic table;

R=Si (CH$_3$)$_3$, substituted or unsubstituted benzyl, and

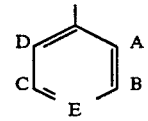

wherein A, B, C, D are the same or different and selected from F, H, NO$_2$ and alkyl and E is endocyclic nitrogen, C-CN or isomers thereof.

3. The process as set forth in claim 1 wherein the ligand of the catalyst precursor is selected from the general, formulae I' and II'

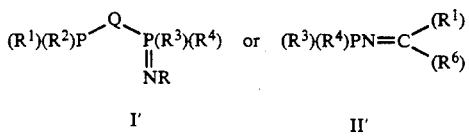

where $R^1$-$R^4$ = same or different, substituted or unsubstituted, alkyl, aryl, alkoxide, aryloxide, amino, or thiol group Q = $(CH_2)_n$, n = 1-5, benzene ring connected to the P atoms in the ortho positions, an olefin connected to the P atoms in the cis position, C(H)CH$_3$ and a substituted amine N($R^7$)

$R^6$ = hydrogen or the substituents as defined for $R^1$-$R^4$ above $R^7$ = substituted or unsubstituted aryl or alkyl R = Si(CH$_3$)$_3$, substituted or unsubstituted benzyl, and

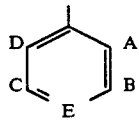

where A,B,C,D are the same or different and selected from F,H,NO$_2$ and alkyl, E is endocyclic nitrogen C-CN or isomers thereof.

4. The process as set forth in claim 3 wherein the source of the group VIIIB transition metal is a Rh(I) halogen diolefin complex.

5. The process as set forth in claim 1, wherein the group VIIIB transition metal is Rh(I).

6. The process as set forth in claim 1, wherein the solvent includes ethanol.

7. The process as set forth in claim 1, wherein the promoter is triethylamine or diethylamine or mixtures thereof.

8. The process as set forth in claim 3 wherein the source of the group VIIIB transition metal is a Rh(I) halogen diolefin complex selected from [RhCl(cod)]$_2$, [RhCl(nbd)]$_2$ or [RhCl(C$_2$H$_4$)$_2$]$_2$, where cod = 1,5 cyclooctadiene and nbd = norbornadiene.

9. The process as set forth in claim 2, wherein the solvent includes ethanol.

10. The process as set forth in claim 3, wherein the solvent includes ethanol.

11. The process as set forth in claim 2, wherein the promoter is triethylamine or diethylamine or mixtures thereof.

12. The process as set forth in claim 3, wherein the promoter is triethylamine or diethylamine or mixtures thereof.

13. The process of claim 2, wherein the Group VIIIB transition metal is Rh(I).

14. The process of claim 3, wherein the Group VIIIB transition metal is Rh(I).

15. The process of claim 6, wherein the Group VIIIB transition metal is Rh(I).

16. The process of claim 7, wherein the Group VIIIB transition metal is Rh(I).

17. The process of claim 1, wherein the source of the Group VIIIB transition metal is an Rh(I) halogen diolefin complex.

18. The process of claim 2, wherein the source of the Group VIIIB transition metal is an Rh(I) halogen diolefin complex.

* * * * *